United States Patent [19]

Still

[11] 4,339,388

[45] Jul. 13, 1982

[54] SYNTHESIS OF PERIPLANONE-B

[76] Inventor: W. Clark Still, 560 Riverside Dr., New York, N.Y. 10027

[21] Appl. No.: 142,643

[22] Filed: Apr. 22, 1980

[51] Int. Cl.³ .......................................... C07D 493/10
[52] U.S. Cl. ................................. 549/332; 568/377; 556/436
[58] Field of Search .................................. 260/348.55

[56] References Cited

PUBLICATIONS

Still, Jour. Am. Chem. Soc., vol. 99 (1977), pp. 4186–4187; 4836–4838.
Still, Jour. Am. Chem. Soc., vol. 101 (Apr. 25, 1979), pp. 2493–2495.
Adams et al., Jour. Am. Chem. Soc., vol. 101 (Apr. 25, 1979), pp. 2495–2498.
C. J. Persoons et al., Tetrahedron Letters, vol. 24 (1976), pp. 2055–2058.

*Primary Examiner*—Norma S. Milestone
*Attorney, Agent, or Firm*—Brooks, Haidt, Haffner & Delahunty

[57] ABSTRACT

A synthesis of periplanone-B, a female sex pheromone of the American cockroach, *P. americana*, is described. Novel compounds which are useful as intermediates in the synthesis of periplanone-B are described including the precursor alcohol, periplanol-B.

3 Claims, 3 Drawing Figures

90 MHZ NMR SPECTRUM OF COMPOUND 9 IN CDCL₃

SYNTHESIS OF PERIPLANONE-B

This invention relates to certain novel germacranoids and precursors used in the synthesis of periplanone-B, a female sex pheromone of the American cockroach, *Periplaneta americana.*

Females of the species *Periplaneta americana* have long been known to produce an extraordinarily potent sex pheromone. Unlike the long range sex attractants which help many insects to locate a receptive mate, the cockroach pheromone acts over relative short distances and functions largely as a close proximity sex excitant. Persoons et al reported the results of a massive cockroach rearing and extraction program which led to the isolation of two extremely active compounds, periplanone-A and periplanone-B. The latter material was characterized spectrally and assigned a germacranoid structure. (stereochemistry unknown). See Tetrahedron Lett., No. 24,2055 (1976). The structure proposed by Persoons et al has now been confirmed and the stereochemistry should be represented as

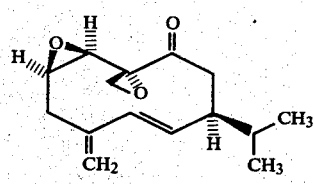
(1)

Because of the interest in the pheromone as a potential lure for the pest, *Periplaneta americana*, a means for producing the compound periplanone-B in relatively large quantities is highly desirable, and it is accordingly a principal object of this invention to provide a synthesis of periplanone-B and in particular to provide valuable intermediate compounds from which periplanone-B can be synthesized.

In accordance with this invention one synthetic route commences with the known compound 5-hydroxymethyl-2-cyclohexen-1-one. (See Van Tamelen et al, J. Am. Chem. Soc., 78, 4405 (1956)). The hydroxyl group is protected, for example by reaction with chloroethyl ether to form the ethoxy ethyl ether. The protected enone is then subjected to kinetic aldolization, (See Stork et al, J. Org. Chem., 39, 4559 (1974)), and in situ acetylation to form the allyl acetate:

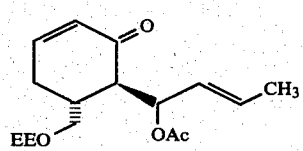
(2)

The substituted enone (2) is then further protected, for example, by addition of Me₃SnLi and Me₃SiCl to give the beta-stannyl enol silyl ether;

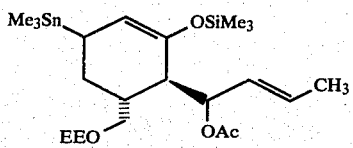
(3)

The allyl acetate is reacted with Me₂CuLi and the stannyl and silyl ether substituents are then removed by oxidation to yield the disubstituted cyclohexenone:

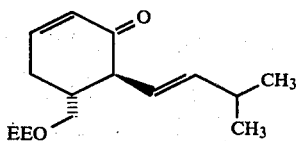
(4)

Compound (4) is then provided with an additional vinyl substituent by the addition of vinyllithium and is subjected to an oxy-Cope rearrangement to form the cyclodecadienone:

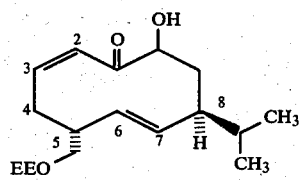
(5)

The ring hydroxyl group of compound (5) is then protected, for example by silylation. Removal of the protection at the original hydroxymethyl substituent and elimination of that hydroxyl group yields the compound:

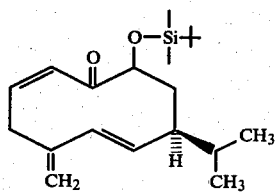
(6)

Compound (6) is then epoxidized to give a mixture of epoxy ketones of which the major component is the desired isomer:

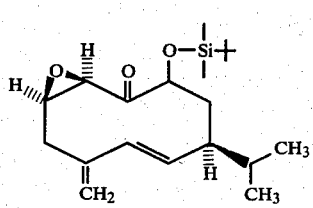
(7)

Isomer (7) is purified and treated with a methylene transfer reagent to give the bisepoxide:

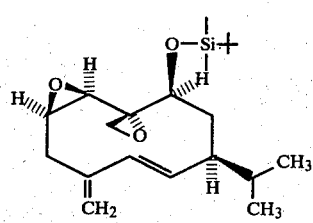
(8)

which upon removal of the hydroxyl protection leaves the free alcohol:

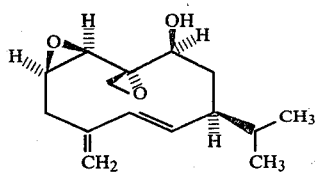

The alcohol is then oxidized to produce a compound having the structure depicted at (1).

Comparison of the synthesized (±) Compound (1) with natural periplanone-B by NMR, IR and mass spectra show the substances to be identical. Bioassay of the synthesized (±) compound (1) show it to be as active as periplanone-B within experimental error.

An alternate process involves hydroxyl inversion of the free alcohol, compound 9, (see Bose et al, Tetrahedron Lett., 1619 (1973)) to the epimeric alcohol:

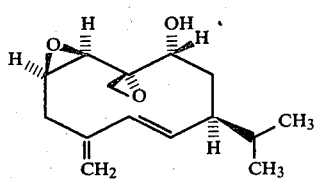

Compound (10) is particularly useful in the synthesis of periplanone-B since it is rapidly and cleanly oxidized under the same conditions as compound (9).

EXAMPLE I

Figure 1:
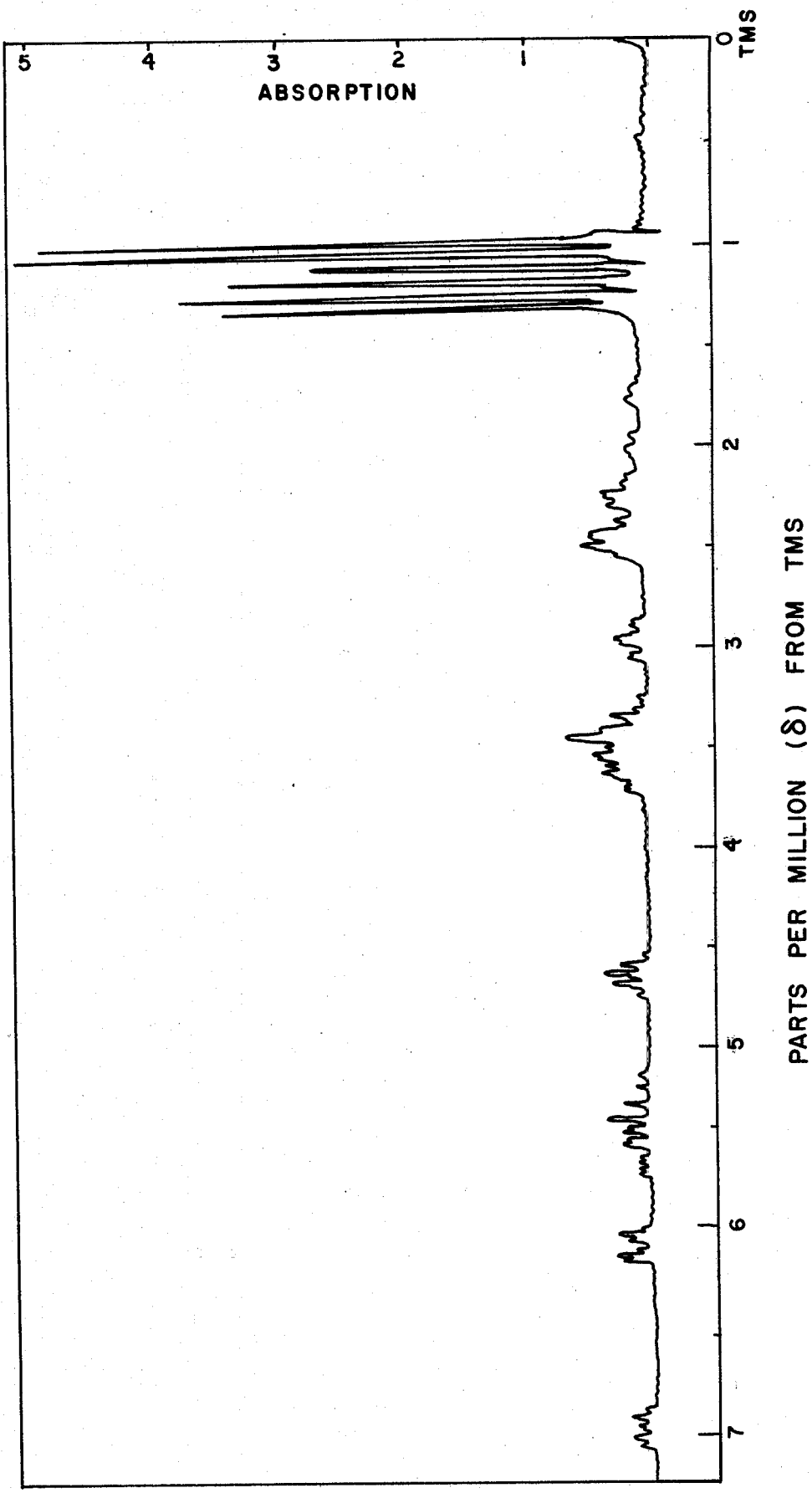
FIG. 1 is an NMR spectrum of the allyl acetate vinyl carbinole compound 4.

PROTECTION OF STARTING MATERIAL 2.0 grams of 5-(hydroxymethyl)-2-cyclohexen-1-one were dissolved in 25 ml. methylene dichloride. 3.03 grams of N,N-dimethylaniline were added and cooled to 0° C. 2.44 grams of chloroethyl ethyl ether were added with stirring. After five minutes the reaction mass was stripped at reduced pressure, and the residue was washed directly twice with 0.5 N hydrochloric acid, dried with $K_2CO_3$ and stripped to recover 2.9 grams of a light yellow oil. The recovered material was purified by flash chromatography (see Still et al, J. Org. Chem, 43, 2923 (1978)) on silica gel with 20% ethyl acetate:petroleum ether as the solvent-eluant. Thin layer chromatogram (Silica Gel, 50% ethyl acetate:Pentane) $R_f=0.70$.

EXAMPLE II

FORMATION OF COMPOUND THREE 1.1 m.mole of lithium diisopropylamide in 10 ml tetrahydrofuran at 0° C. were treated with one m.mole of the product of Example I dissolved in 0.6 ml. tetrahydrofuran added drop-wise over a period of about two minutes. The mixture was stirred for five minutes, cooled to −78° C., and 1.05 m.mole (0.085 ml.) of crotonaldehyde were added and stirred for five minutes. 1.05 m.mole of acetic anhydride were then added. Stirring was ccontinued for an additional twenty minutes to form compound (2).

Enone protection was then provided for the ring olefin bond and the oxygen substituent by addition of trimethylstannyllithium and silylation. The trimethylstannyllithium was prepared by adding 1.05 m.mole of methyllithium to 1.1 m.mole of hexamethyldistannane in 2 ml. tetrahydrofuran under a nitrogen atmosphere. As soon as the trimethylstannyllithium addition was complete at −78° C. (approximately 5 min.), 0.20 ml. of trimethylsilylchloride was added and stirred for an additional 15 minutes. The reaction mass was then poured into petroleum ether, washed with water, and dried ($Na_2SO_4$). The mixture was then stripped (1 mm Hg) to yield a pale yellow oil (651 mg.). IR and NMR spectra confirmed the presence of the acetate group and the formation of the enol ether as indicated in compound 3. Thin layer chromatogram (Silica Gel, 5% ethyl acetate:Pentane) $R_f=0.77$.

EXAMPLE III

FORMATION OF COMPOUND FOUR

The yellow oil product of Example II (compound 3) in 1.5 ml ethyl ether was mixed into two m.mole of lithiumdimethyl cuprate in 10 ml. ethyl ether at 0° C. and stirred for 20 minutes. The mixture was then poured into petroleum ether, washed three times with water and then oxidized to remove the stannyl enol silyl ether by addition of 0.2 gm. metachloroperoxybenzoic acid. The mixture was then shaken vigorously for one minute, washed thoroughly with saturated sodium sulfite and saturated sodium bircarbonate solutions and then stripped to 400 mg. of a pale yellow oil (compound 4). Thin layer chromatogram (Silic Gel, 20% ethyl acetate:pentane) $R_f=0.55$.

The stereochemistry indicated in compound 4, depicted above, follows from the NMR of the compound which shows a diaxial relationship between the protons at C5 and C6 and a typical trans coupling constant for the vinyl hydrogens at C7 and C8.

EXAMPLE IV

RING EXPANSION TO COMPOUND FIVE

Ethereal vinyllithium was prepared by forming a mixture of 1 gm. (4.4 mole) of tetravinyl tin in 50 ml. anhydrous ethyl ether at 0° C., under a nitrogen atmosphere, to which, after stirring, were added 12 m.mole of n-butyllithium. After fifteen minutes the mixture was cooled to −78° C., and 2.5 gm (9.5 m.mole) of compound 4 dissolved in 10 ml. ethyl ether were added drop-wise with stirring. After ten minutes the mixture was poured into petroleum ether, washed with water, dried with sodium sulfate and stripped to yield a light yellow oil. Thin layer chromatogram (silica Gel, 20% ethyl acetate:Pentane) $R_f=0.75$.

This crude vinyl carbinol dissolved in 25 ml. tetrahydrofuran was added to pentane washed potassium hydrofuran dispersed in 10 ml. tetrahydrofuran. Considerable evolution of gas occurred. 1 gm. of a commercially available cyclic polyether (18-Crown-6) was added, and the mixture refluxed for one hour under a nitrogen atmosphere. The mixture was then cooled to −78° C., stirred vigorously and injected with 3 ml. of trimethylsilyl chloride in a single portion. The mixture, which had been dark, lightened, and a white precipitate was deposited. The mixture was stirred for another five minutes and poured into petroleum ether. This was carefully washed with water twice and 3.0 gm of 85% metachloroperoxybenzoic acid was then added and the mixture shaken vigorously for sixty seconds. The mixture was then washed thoroughly with saturated solutions of sodium sulfite and sodium bicarbonate, dried (sodium sulfate) and stripped to a yellow oil. (compound 5). The yield of 1.6 gm. was approximately 52%. Thin layer chromatogram (Silica gel, 20% ethyl acetate:pentane) $R_f=0.30$.

EXAMPLE V

PREPARATION OF COMPOUND SIX (Compound 5)

300 mg. (1 m.mole) of the product of Example IV and 150 mg. of imidazole were mixed in N,N-dimethylformamide. 180 mg. (1.2 m. mole) of dimethyl-t-butylsilyl chloride were added to provide hydroxyl protection. After 12 hours the mixture was partitioned between petroleum ether and water, washed with water, dried with $Na_2SO_4$) and stripped to yield 438 mg. of a pale yellow oil. Thin layer chromatogram (Silica gel, 20% ethyl acetate:pentane) $R_f=0.70$.

90 mg of this product were dissolved in a mixture of 0.5 ml. acetic acid, 0.25 ml. methyl alcohol and 0.2 ml. water to remove the ethoxy ethyl protection on the hydroxymethyl substituent. This mixture stood for about one hour at room temperature after which the reaction was complete. Brine and potassium carbonate were added, the mixture was extracted three times with ethyl ether, and the extract was stripped to yield a light yelow oil. This oil was purified by flash chromatography using a 30% ethyl acetate:petroleum ether solvent-eluant for a yield of 44 mg. Thin layer chromatogram (Silica gel, 20% ethyl acetate:pentane) $R_f=0.20$. 25 mg. of the purified oil, 28 mg of ortho-nitrophenyl-selenocyanate in 0.5 ml. tetrahydrofuran were stirred together at 10° C., and 30 µl. of tributylphosphine was added. After 10 minutes at room temperature the mixture was partitioned between water and petroleum ether and stripped to a brown oil, from which 29 mg of a yellow oil were purified by flash chromatography on silica gel with 15% ethyl acetate-petroleum ether.

1 ml. Tetrahydrofuran and 0.25 ml. of 30% hydrogen peroxide were added to the yellow oil. The mixture was allowed to stand for 18 hours and then partitioned between water and petroleum ether, stripped to a yellow oil which was purified by flash chromatography using 5% ethyl acetate-petroleum ether on silica gel for a yield of 19 mg. of the silylated methylene substituted compound 6. Thin layer chromatogram (silica gel, 10% ethyl acetate:pentane) $R_f=0.75$.

EXAMPLE VI

EPOXIDATION TO COMPOUND 7

100 ul. of 6 M potassium hydride were washed with petroleum ether and suspended in 5 ml. of anhydrous tetrahydrofuran under a nitrogen atmosphere and cooled to 0° C. The suspension was stirred and 200 µl. of tertiary butylhydroperoxide were added with evolution of gas. After 10 minutes at 0° C. the mixture was cooled to −20° C., and 110 mg. of compound 6 in 1 milliliter of tetrahydrofuran were added. The resultant mixture was stirred at −20° C. for 45 minutes. Petroleum ether was added, and the mixture was washed with water, dried (sodium sulfate) and stripped to a crystalline solid (compound 7) (MP=113.5°–114° C.) Thin layer chromatogram (Silica gel, 5% ethyl acetate:pentane) $R_f=0.40$.

EXAMPLE VIII

FORMATION OF THE BISEPOXIDE, COMPOUND 8

75 ul. of a 6 M suspension of potassium hydride in mineral oil was washed with pentane and suspended in 1 ml. of tetrahydrofuran under nitrogen. To this suspension was added 1 ml. of anhydrous dimethylsulfoxide. After the gas evolution ceased, the mixture was cooled to −5° C., and 150 mg of trimethylsulfonium iodide was added. After five minutes, 130 mg. of compound 7 in 0.5 ml. tetrahydrofuran was added. After stirring for ten minutes, petroleum ether was added and the mixture was washed with water twice. Chromatography on silica gel with 4% ethyl acetate; petroleum ether gave the bisepoxide, compound 8. Yield=93 milligrams. Thin layer chromatogram (silica gel, 5% acetate:pentane) $R_f=0.60$.

EXAMPLE IX

DEPROTECTION TO GIVE THE FREE ALCOHOL, COMPOUND 9

To a solution of 0.5 ml of 1 molar tetrabutylammonium fluoride was added 9 mg of the bisepoxide 8. After ten minutes, aqueous sodium chloride was added and the mixture was extracted with ethyl ether four times. The ethereal extracts were dried with sodium sulfate and stripped to the free alcohol, compound 9. The product weighed 8 milligrams and was a crystalline solid (mp=81° C.). Thin layer chromatogram (silica gel, 20% ethyl acetate: pentane) $R_f=0.20$.

EXAMPLE X

OXIDATION TO PERIPLANONE-B

To a mixture of 400 ul. of methylene chloride and 35 ml. of pyridine was added 22 mg. of dry chromium trioxide. The resulting red solution was stirred for ten minutes, and 8 mg. of the free alcohol of Example IX was added. After ten minutes, ethyl ether was added, and the mixture was filtered through silica gel. Removal of the solvent gave an oily product (periplanone-B) (6.5 milligrams). Thin layer chromatogram (silica gel, 20% ethyl acetate:pentane) $R_f=0.70$.

EXAMPLE XI

PREPARATION OF THE EPIMERIC ALCOHOL, COMPOUND 10.

5 mg. of synthetic periplanone-B (above) was dissolved in 0.5 ml. of ethanol and treated at 0° C. with 25 mg. of sodium borohydride. After ten minutes, water was added and the mixture was extracted with ethyl ether three times. The extracts were dried (sodium sulfate) and the solvents were removed to yield an oil. Thin layer chromatogram (silica gel, 20% ethyl acetate:pentane) $R_f=0.30$.

This oily alcohol was oxidized to periplanone-B by the method described above in Example X.

Figure 2:
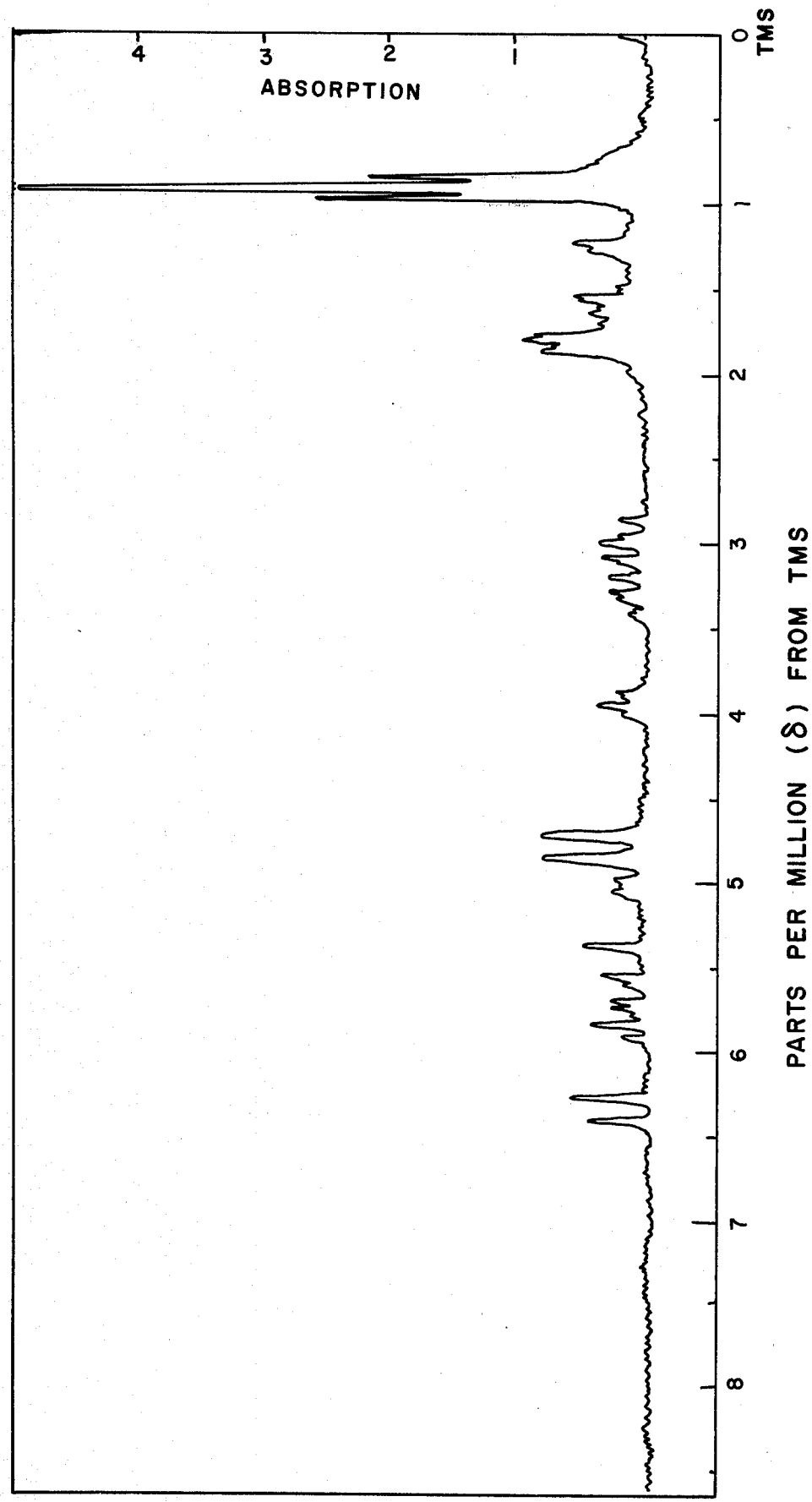
FIG. 2 is an NMR spectrum of the silylated compound 6.
Figure 3:
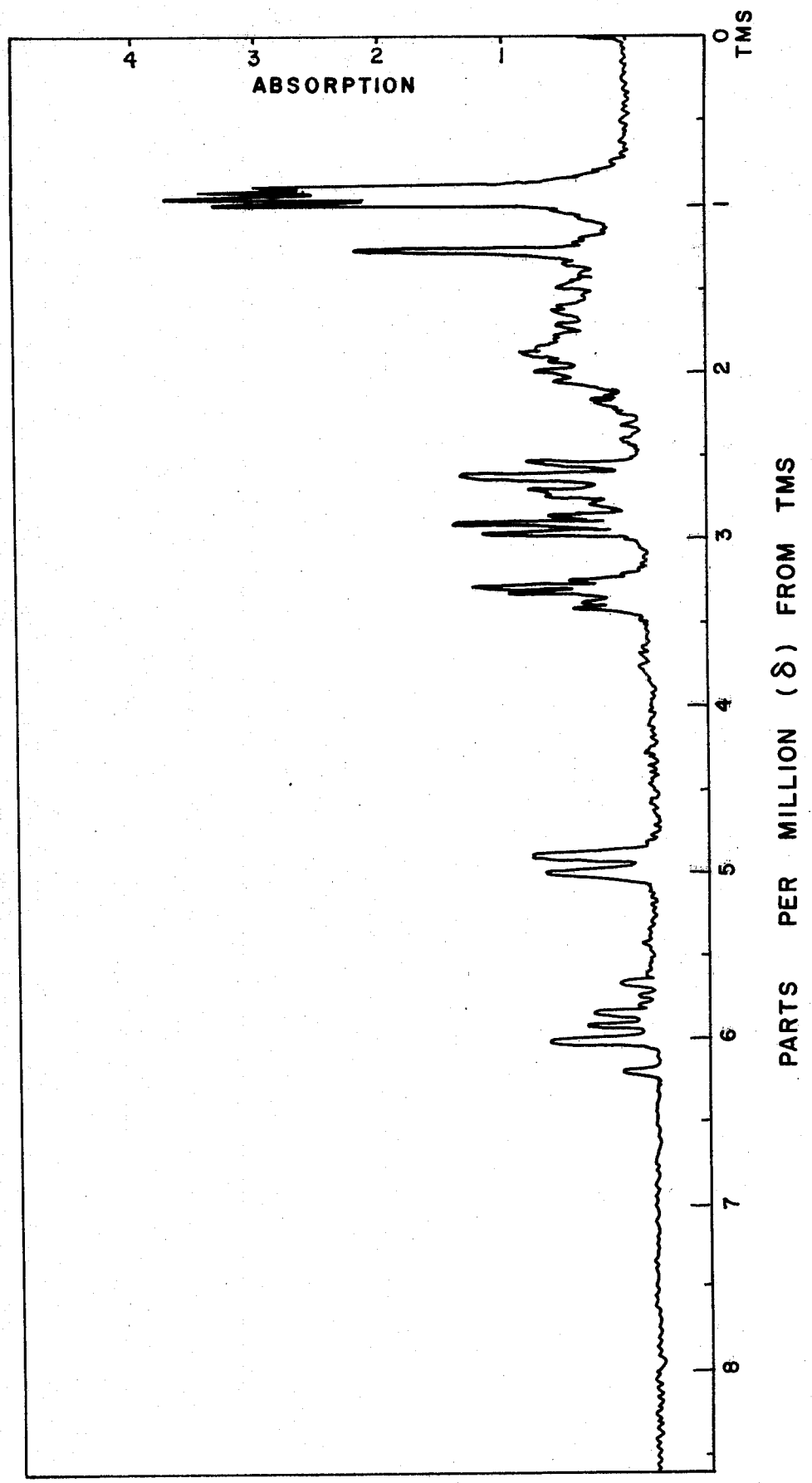
FIG. 3 is an NMR spectrum of the free alcohol, compound 9. de

In the appended drawings:

Fig. 1 is an NMR spectrum of the allyl acetate vinyl carbinole compound 4;

Fig. 2 is an NMR spectrum of the silylated compound 6; and
Fig. 3 is an NMR spectrum of the free alcohol, compound 9/
I claim:
1. An alcohol selected from the group consisting of
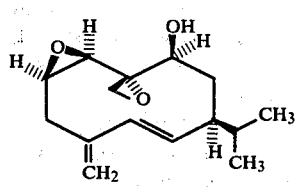
AND
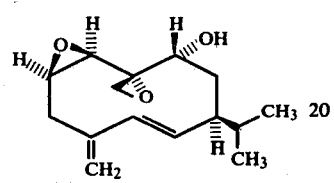
2. An alcohol according to claim 1 which as the structural formula:
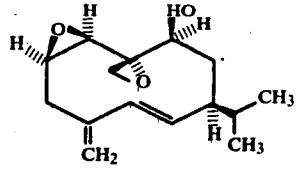
3. An alcohol according to claim 1
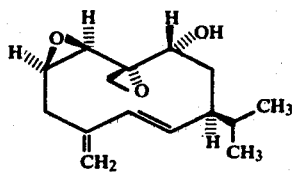
* * * * *